US012648919B2

(12) United States Patent
Son et al.

(10) Patent No.: US 12,648,919 B2
(45) Date of Patent: Jun. 9, 2026

(54) ANTICOCCIDIAL COMPOSITION COMPRISING COUMARIC ACID AND USE THEREOF

(71) Applicant: CJ CHEILJEDANG CORPORATION, Seoul (KR)

(72) Inventors: Kyuyeol Son, Seoul (KR); Min Ah Park, Seoul (KR); Kyung Min Lee, Seoul (KR); Hwi-Jea Kim, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 526 days.

(21) Appl. No.: 18/024,943

(22) PCT Filed: Mar. 4, 2022

(86) PCT No.: PCT/KR2022/003072

§ 371 (c)(1),
(2) Date: Mar. 6, 2023

(87) PCT Pub. No.: WO2022/186648

PCT Pub. Date: Sep. 9, 2022

(65) Prior Publication Data

US 2024/0299324 A1 Sep. 12, 2024

(30) Foreign Application Priority Data

Mar. 5, 2021 (KR) ........................ 10-2021-0029733

(51) Int. Cl.

| | |
|---|---|
| ***A01N 43/00*** | (2006.01) |
| ***A01N 43/46*** | (2006.01) |
| ***A61K 9/00*** | (2006.01) |
| ***A61K 31/192*** | (2006.01) |
| ***A61K 31/55*** | (2006.01) |
| ***A61P 33/02*** | (2006.01) |

(52) U.S. Cl.

CPC .......... *A61K 31/192* (2013.01); *A61K 9/0056* (2013.01); *A61P 33/02* (2018.01)

(58) Field of Classification Search

None

See application file for complete search history.

(56) References Cited

U.S. PATENT DOCUMENTS

| | | | |
|---|---|---|---|
| 2003/0091589 | A1 | 5/2003 | Dawson et al. |
| 2015/0273004 | A1 | 10/2015 | Thangavel et al. |
| 2019/0150478 | A1 | 5/2019 | Friesen et al. |

FOREIGN PATENT DOCUMENTS

| | | | |
|---|---|---|---|
| JP | 2003-504327 | A | 2/2003 |
| JP | 2005-535325 | A | 11/2005 |
| JP | 2006-314313 | A | 11/2006 |
| JP | 2011-205952 | A | 10/2011 |
| KR | 10-2016-0145328 | A | 12/2016 |
| KR | 10-2018-0083818 | A | 7/2018 |
| WO | 2019/244929 | A1 | 12/2019 |
| WO | 2020/152673 | A1 | 7/2020 |
| WO | 2021/016141 | A1 | 1/2021 |

OTHER PUBLICATIONS

Abbas et al., "In vivo anticoccidial effects of *Beta vulgaris* (sugar beet) in broiler chickens," Microbial Pathogenesis, Accepted Manuscript (2017).
Abbas et al., "In vivo anticoccidial effects of *Beta vulgaris* (sugar beet) in broiler chickens," Microbial Pathogenesis, 111: 139-144 (2017).
Abbas et al., "Botanicals: an alternative approach for the control of avian coccidiosis," Worlds Poultry Science Journal, 68: 203-215 (2012).
Williams, "A compartmentalised model for the estimation of the cost of coccidiosis to the world's chicken production industry," International Journal for Parasitology, 29(8):1209-1229 (1999).
Johnson et al., "Anticoccidial drugs: Lesion scoring techniques in battery and floor-pen experiments with chickens," Experimental Parasitology, 28: 30-36 (1970).
De Pablos et al., "Anticoccidial activity of maslinic acid against infection with Eimeria tenella in chickens," Parasitology Research, 107: 601-604 (2010).
International Search Report issued in corresponding International Patent Application No. PCT/KR2022/003072 dated Jun. 13, 2022.
Office Action issued in corresponding Japanese Patent Application No. 2023-519072 dated Feb. 16, 2024.
Office Action issued in corresponding Korean Patent Application No. 10-2021-0029733 dated Mar. 11, 2024.
Lopes et al., "Trypanocidal Mechanism of Action and in silico Studies of p-Coumaric Acid Derivatives," International Journal of Molecular Sciences, vol. 20: 5916, 2019, pp. 1-21.
Anaya-Esparza et al., "Bell Peppers (*Capsicum annum* L.) Losses and Wastes: Source for Food and Pharmaceutical Applications", Molecules, vol. 26, 2021, pp. 1-23.
Lee et al., "Effect of Dietary Curcuma, Capsicum, and Lentinus on Enhancing Local Immunity against Eimeria acervulina Infection", Japan Poultry Science Association, J. Poult. Sci., vol. 47, 2010, pp. 89-95.
Muthamilselvan et al., "Herbal Remedies for Coccidiosis Control: A Review of Plants, Compounds, and Anticoccidial Actions", Hindawi Publishing Corporation, Evidence-Based Complementary and Alternative Medicine, vol. 2016, 2016, pp. 1-20, XP-002786334.
Ovando-Martínez et al., "Simulated Gastrointestinal Digestion, Bioaccessibility and Antioxidant Capacity of Polyphenols from Red Chiltepin (*Capsicum annuum* L. Var. *glabriusculum*) Grown in Northwest Mexico", Plant Foods for Human Nutrition, vol. 73, 2018, pp. 116-121.

(Continued)

*Primary Examiner* — Layla Soroush
(74) *Attorney, Agent, or Firm* — Morgan, Lewis & Bockius LLP

(57) ABSTRACT

The present application relates to an anticoccidial composition comprising coumaric acid and use thereof. A composition comprising coumaric acid and/or a salt thereof, according to an embodiment, has excellent effects of inhibiting the cell penetration of protozoa that can induce coccidiosis and/or inhibiting the proliferation of the protozoa in cells, has excellent effects of preventing, ameliorating and treating coccidiosis in vivo, and remarkably reduces oocyst excretion in feces, thus being able to reduce secondary coccidiosis infection.

16 Claims, 1 Drawing Sheet

Specification includes a Sequence Listing.

(56) References Cited

OTHER PUBLICATIONS

Extended European Search Report issued in corresponding European Patent Application No. 22763629.7, dated Dec. 5, 2024.

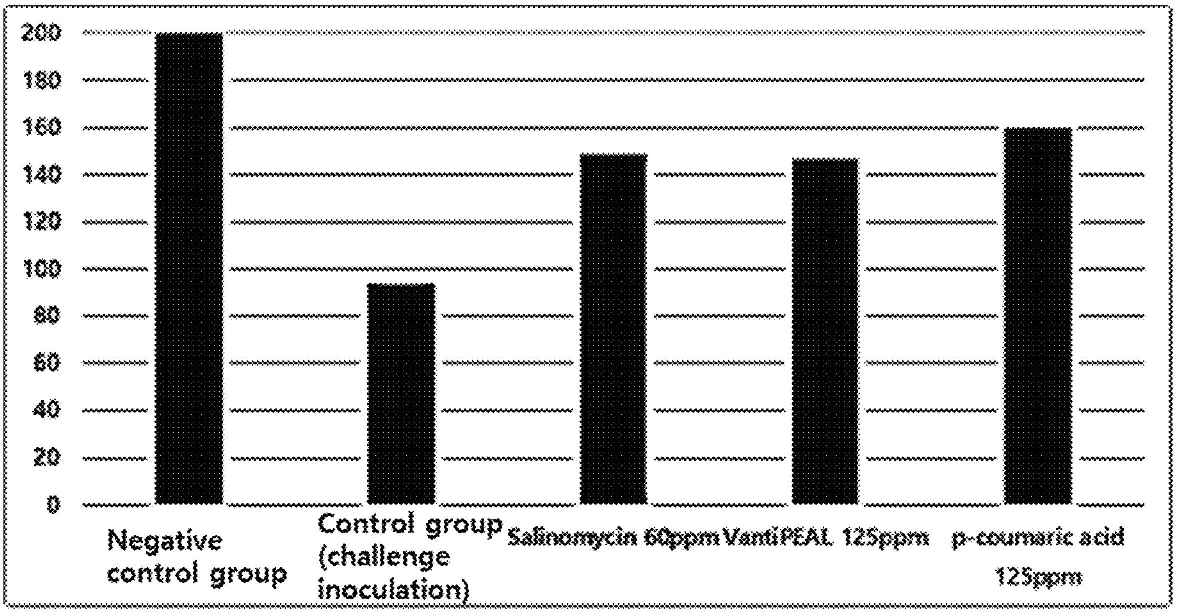
200
180
160
140
120
100
80
60
40
20
0
Negative control group
Control group (challenge inoculation)
Salinomycin 60ppm
VantiPEAL 125ppm
p-coumaric acid 125ppm

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: synthetic_E.tenella ITS-1_forward

<400> SEQUENCE: 1
tggaggggat tatgagagga 20

<210> SEQ ID NO 2
<211> LENGTH: 20
<212> TYPE: DNA
<213> ORGANISM: Artificial Sequence
<220> FEATURE:
<223> OTHER INFORMATION: synthetic_E.tenella ITS-1_reverse

<400> SEQUENCE: 2
caagcagcat gtaacggaga 20

<210> SEQ ID NO 3
<211> LENGTH: 22
<212> TYPE: DNA
<213> ORGANISM: Artificial Sequence
<220> FEATURE:
<223> OTHER INFORMATION: synthetic_E.acervulina ACE_forward

<400> SEQUENCE: 3
gcagtccgat gaaaggtatt tg 22

<210> SEQ ID NO 4
<211> LENGTH: 22
<212> TYPE: DNA
<213> ORGANISM: Artificial Sequence
<220> FEATURE:
<223> OTHER INFORMATION: synthetic_E.acervulina ACE_reverse

<400> SEQUENCE: 4
gaagcgaaat gttaggccat ct 22

ANTICOCCIDIAL COMPOSITION COMPRISING COUMARIC ACID AND USE THEREOF

A computer readable text file, entitled "SequenceListing.txt," created on or about Feb. 15, 2023 with a file size of 1,131 bytes contains the sequence listing for this application and is hereby incorporated by reference in its entirety.

CROSS-REFERENCE TO RELATED APPLICATION(S)

The present application claims the benefit of the priority based on Korean Patent Application No. 10-2021-0029733 filed on Mar. 5, 2021, and the entire contents disclosed in the document of the corresponding Korean patent application are incorporated as a part of the present description.

TECHNICAL FIELD

The present application relates to an anticoccidial composition comprising a coumaric acid and/or a salt thereof and uses thereof.

BACKGROUND ART

Coccidiosis is an intestinal-related disease caused by a protozoan parasite belonging to the phylum apicomplexan called *Eimeria*, and when affected with coccidiosis, symptoms of digestive disorders, diarrhea and weight loss are shown, and furthermore, death of livestock is caused, and therefore, it has a major economic impact on farms around the world (Williams R B. A compartmentalised model for the estimation of the cost of coccidiosis to the world's chicken production industry. Int J Parasitol. 1999; 29(8): 1209-1229).

Over the past few years, many researchers have developed anticoccidial agents such as ionophores or chemically synthetic compounds, which can prevent oocyst cell wall formation or asexual and sexual reproduction of protozoa as therapeutic agents for treating coccidiosis. However, side effects such as appearance of protozoa with drug resistance due to the long-term use of a shuttle program that alternately treats the ionophores and chemically synthetic compounds and the like occurred.

In particular, antibiotics accumulated in animals due to misuse and abuse of antibiotics are a serious problem as humans consume antibiotics through meat, and therefore, antibiotic administration are being banned in many countries around the world due to the problem of antibiotic residues in livestock products. Therefore, there is an urgent need to develop and research alternatives to conventional anticoccidial agents that exhibit side effects such as emergence and internal residue of strains resistant to drugs.

PRIOR ART

Patent Document (Patent document 1) U.S. Patent Publication No. 2008-0160000

DISCLOSURE

Technical Problem

One embodiment of the present application provides a use of coumaric acid and/or a salt thereof for using in preventing or alleviating coccidiosis.

Another embodiment of the present application provides a feed composition for preventing or alleviating coccidiosis, comprising coumaric acid and/or a salt thereof as an active ingredient.

Other embodiment of the present application provides a pharmaceutical composition for preventing or treating coccidiosis, comprising coumaric acid and/or a pharmaceutically acceptable salt thereof as an active ingredient.

Other embodiment of the present application provides a use of coumaric acid and/or a salt thereof for the manufacture of a composition (for example, feed composition, pharmaceutical composition) for preventing, alleviating and/or treating coccidiosis.

Other embodiment of the present application provides a method for preventing, alleviating or treating coccidiosis, comprising a step of administering the composition (for example, the feed composition, the pharmaceutical composition, and/or the antiprotozoal composition) to an animal except for human.

Other embodiment of the present application provides a use of coumaric acid and/or a salt thereof for using in antiprotozoan against an *Eimeria* sp. protozoan (for example, *Eimeria* sp. protozoa killing; and/or cell invasion and/or propagation inhibition of *Eimeria* sp. protozoa).

Other embodiment of the present application provides an antiprotozoal composition against an *Eimeria* sp. protozoan, comprising coumaric acid and/or a salt thereof as an active ingredient.

Other embodiment of the present application provides a use of coumaric acid and/or a salt thereof for the manufacture of an antiprotozoal composition an *Eimeria* sp. protozoan.

Other embodiment of the present application provides a method for preventing, alleviating and/or treating coccidiosis, or a pest control method of an *Eimeria* sp. protozoan, comprising a step of administering coumaric acid and/or a salt thereof to an animal (for example, subject in need of protozoal pest control, or animal except for human). In the present description, the protozoal pest control means the antiprotozoal action inclusively, and for example, it may mean the *Eimeria* sp. protozoa killing; and/or cell invasion and/or propagation inhibition of *Eimeria* sp. protozoa, and the like, but not limited thereto.

In one embodiment, the coumaric acid may have the structure of Chemical formula 1 below.

[Chemical formula 1]

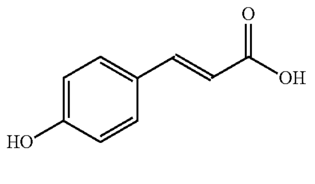

Technical Solution

The composition comprising a coumaric acid and/or a salt thereof according to one embodiment may have excellent anticoccidial activity and/or antiprotozoal activity against protozoa inducing coccidiosis.

In the present application, the excellent anticoccidial efficacy (activity, effect) may mean at least one (for example, any one, 2 or more kinds, 3 or more kinds, or all) selected from the group consisting of the following (1) to (5):

(1) a higher anticoccidial index (ACI) compared to the control group;
(2) reduced mortality, lesion score (for example, appendix lesion score) and/or fecal oocyst excretion amount compared to the control group when administered to a coccidiosis-induced animal subject;
(3) inhibition of weight loss by induction of coccidiosis;
(4) higher insecticidal activity against protozoa which induce coccidiosis compared to the control group; and
(5) a higher inhibitory effect of cell invasion of protozoa which induce coccidiosis and/or propagation of the protozoa in cells compared to the control group.

In the present application, the control group may mean a negative control group (a group in which nothing is treated or water and/or a buffer treatment group) and/or a positive control group comprising a conventionally known anticoccidial agent (for example, diclazuril, salinomycin and/or gallic acid).

The composition according to one embodiment may have at least one (for example, one or more kinds, 2 or more kinds, 3 or more kinds, 4 or more kinds, 5 or more kinds or all of 6 kinds) characteristics selected from the group consisting of the following (1) to (6), and its characteristic may be more excellent than the control group:
(1) excellent anticoccidial activity;
(2) excellent antiprotozoal effect against protozoa which induce coccidiosis;
(3) excellent acid resistance;
(4) excellent heat resistance;
(5) excellent in vivo stability and/or safety; and
(6) excellent weight gain improvement effect.

The composition according to one embodiment has excellent acid resistance and/or heat resistance, thereby maintaining the excellent anticoccidial activity for a long period of time when administered to a body, and has in vivo stability, thereby maintaining the excellent anticoccidial activity even in an environment in various temperature and/or pH ranges, and it may be applicable for various products (for example, feed additives), and the storage stability may be excellent.

The composition according to one embodiment is not absorbed by other tissue and organs (for example, blood, liver, kidney and/or spleen, etc.) other than intestines when administered in vivo, and therefore, has a low residue in a body, and thus, it may have excellent safety in vivo.

In one embodiment, the excellent weight gain improvement effect may mean an excellent effect of increasing a body weight of a subject when administered to the subject, and in one embodiment, the weight gain may mean daily weight gain, and the subject may be a subject in which coccidiosis is induced.

The composition according to one embodiment exhibits the anticoccidial activity equivalent or more than conventional known anticoccidial agents (for example, sulfa agents such as sulfaquinoxaline, sulfachloropyrazine and sulfamethazine, polyether ionophore antibiotics such as salinomycin and monensin sodium, amprolium, diclazuril, gallic acid and/or toltrazuril), and comprises a coumaric acid which is a substance that naturally participates in metabolism during the metabolic process and/or a salt thereof, and therefore, it does not cause side effects or drug resistance, and/or it does not remain in a body, so it may be safe to use for a long period of time. The composition according to one embodiment is resistant, but does not remain in a body, so it may be utilized as a substance for preventing, alleviating and/or treating coccidiosis in laying hens as well as broilers. The composition according to one embodiment may significantly reduce the oocyst excretion amount from a subject infected by protozoa causing anti-coccidiosis, so it may reduce the rate of the livestock contamination and/or secondary infection.

In the present application, "prevention" means all acts that inhibit or delay development of disease by administration of the composition according to one embodiment, and "treatment" means all acts which improve or beneficially change symptoms of doubt and onset subjects of disease by administration of the composition according to one embodiment, and "alleviation" may mean all acts which reduce parameters associated with the condition where disease is treated by administration of the composition according to one embodiment, for example, at least the degree of symptoms. The disease may mean coccidiosis.

One aspect may provide a feed composition for preventing or alleviating coccidiosis, comprising coumaric acid and/or a salt thereof (coumaric acid, a salt of coumaric acid, or a combination thereof).

The 'coumaric acid' is one kind of hydroxycinnamic acid, which is a hydroxy derivative of cinnamic acid, and in one embodiment, the coumaric acid may be at least one selected from the group consisting of p-coumaric acid, m-coumaric acid, and o-coumaric acid.

In one embodiment, the coumaric acid may be a trans type and/or cis type. For example, the p-coumaric acid may be trans-p-coumaric acid and/or cis-p-coumaric acid, and the m-coumaric acid may be trans-m-coumaric acid and/or cis-m-coumaric acid, and the o-coumaric acid may be trans-o-coumaric acid and/or cis-o-coumaric acid.

The p-coumaric acid may be named '4-Hydroxycinnamic acid', p-Hydroxycinnamic acid', or 2-(4-hydroxyphenyl) acrylic acid, and may have the molecular formula of $C_9H_8O_3$. In one embodiment, the p-coumaric acid may be represented by the following Chemical formula 1 or Chemical formula 2, or may be a mixture thereof (a compound represented by Chemical formula 1 and a compound represented by Chemical formula 2). In one embodiment, the Cas number of the p-coumaric acid may be Cas No. 501-98-4, Cas No. 7400-08-0, and/or Cas No. 4501-31-9.

[Chemical formula 1]

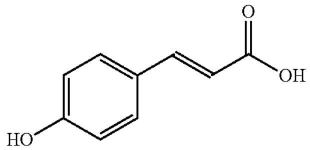

[Chemical formula 2]

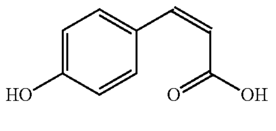

The m-coumaric acid may be named '3-Hydroxycinnamic acid', m-Hydroxycinnamic acid', or 3-(3-hydroxyphenyl) acrylic acid, and may have the molecular formula of $C_9H_8O_3$. In one embodiment, the m-coumaric acid may be represented by the following Chemical formula 3 or Chemical formula 4, or may be a mixture thereof (a compound represented by Chemical formula 3 and a compound represented by Chemical formula 4). In one embodiment, the Cas number of the m-coumaric acid may be Cas No. 14755-02-3, Cas No. 25429-38-3, and/or Cas No. 588-30-7.

[Chemical formula 3]

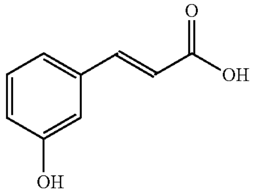

[Chemical formula 4]

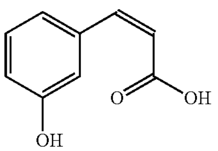

The o-coumaric acid may be named '2-Hydroxycinnamic acid', or 2-hydroxycinnamate, and may have the molecular formula of $C_9H_8O_3$. In one embodiment, the o-coumaric acid may be represented by the following Chemical formula 5 or Chemical formula 6, or may be a mixture thereof (a compound represented by Chemical formula 5 and a compound represented by Chemical formula 6). In one embodiment, the Cas number of the o-coumaric acid may be Cas No. 614-60-8 and/or Cas No. 495-79-4.

[Chemical formula 5]

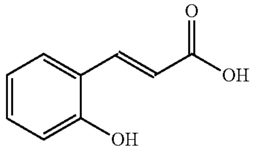

[Chemical formula 6]

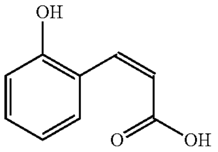

The coumaric acid and/or salt thereof (salt of the coumaric acid) may be obtained by extracting and separating from a natural product (for example, plant) and/or a strain, or may be prepared by a common organic synthesis method, or may be obtained from a manufacturer in the art, but not limited thereto.

The "salt of coumaric acid" in the present application, may mean a physiologically acceptable salt among salts which are substances in which a cation and an anion are combined by electrostatic attraction, and "pharmaceutically acceptable salt" may mean a salt in a form that can be used pharmaceutically and for example, the salt may be at least one selected from the group consisting of metal salts, salts with organic bases, salts with inorganic acids, salts with organic acids, salts with basic or acidic amino acids, and the like. In one embodiment, the metal salt may be at least one selected from the group consisting of alkali metal salts (sodium salt, potassium salt, etc.), alkali earth metal salts (calcium salt, magnesium salt, barium salt, etc.), aluminum salts and the like; and the salt with organic bases may be at least one selected from the group consisting of salts with triethylamine, pyridine, picoline, 2,6-lutidine, ethanolamine, diethanolamine, triethanolamine, cyclohexylamine, dicyclohexylamine, N,N-dibenzylethylenediamine, and the like; and the salts with inorganic acids may be at least one selected from the group consisting of hydrochloric acid, hydrobromic acid, nitric acid, sulfuric acid, phosphoric acid and the like; and the salt with organic acids may be at least one selected from the group consisting of salts with formic acid, acetic acid, trifluoroacetic acid, phthalic acid, fumaric acid, oxalic acid, tartaric acid, maleic acid, citric acid, succinic acid, methane sulfonic acid, benzene sulfonic acid, p-toluene sulfonic acid, and the like; and the salt with basic amino acids may be at least one selected from the group consisting of salts with arginine, lysine, ornithine and the like; and the salt with acidic amino acids may be at least one selected from the group consisting of salts with aspartic acid, glutamic acid, and the like.

In the present application, "coccidiosis" is a disease in which a coccidium protozoan (protozoan which can induce coccidiosis, for example, *Eimeria* sp. coccidium protozoan) parasitizes in the cytoplasm of submucosal tissue in the epithelium of the digestive tract and destroys the epithelium and cause enteritis, and is a protozoal disease that causes economic damage due to weight gain degradation by soft stool, diarrhea and bloody stool and prolongation of the shipping age in a broiler farm. Coccidiosis may be expressed not only in broilers but also in birds and mammals, and specifically, the coccidiosis may infect cattle, rabbits, goats, dogs, cats, mice which are experimental animals, and rats, and the like, and in particular, it may cause fatal damage to poultry such as chickens and the like. In one embodiment, the coccidiosis may include acute coccidiosis, subacute coccidiosis, and chronic coccidiosis and the like. The acute coccidiosis may exhibit bloody stool, energy loss and anemia within 48 hours after infection, and the infected subject may die, and the subacute coccidiosis may exhibit bloody diarrhea and/or anemia symptoms after infection, and the chronic coccidiosis may exhibit symptoms of soft stool and/or body weight loss after diarrhea for 1~2 days after infection.

When an oocyst (cyst) of the coccidium protozoan species matures into a sporulated oocyst at high humidity and temperature, it is infectious, and when the oocyst is excreted in feces after passing through a certain life cycle in a body of a subject, it spreads easily and the life cycle of the oocyst is repeated. It is known that the oocytes (cyst) of the coccidium protozoan species are highly resistant to the external environment, and the cyst wall consists of two layers inside and outside. The outer layer of the cyst wall is a gelatin material that strongly resists external physical pressure and the inner layer is rich in nuclear proteins, so it may strongly resist chemical stimuli, for example, disinfectants. The oocyst of the coccidium protozoan species may comprise 4 sporocysts, and the sporocysts may each comprise 2 sporozoites, and they may be released in a form of sporocyst and sporozoite after infection to an animal in an oocyst form, and proliferate in cells, and the sporozoites that have undergone sexual reproduction and/or asexual reproduction may form an oocyst and be extracted in feces. In one embodiment, the sporozoite may be used in the same meaning as a protozoan, and the sporozoite (protozoan) may cause lesions.

According to one embodiment, the coccidiosis may be caused by an *Eimeria* sp. protozoan. In one embodiment, the *Eimeria* sp. protozoan may be at least one selected from the group consisting of *Eimeria acervulina, Eimeria tenella, Eimeria maxima, Eimeria necatrix, Eimeria brunetti, Eimeria hagani, Eimeria mitis, Eimeria praecox, Eimeria mivati, Eimeria aurati, Eimeria baueri, Eimeria lepidosirenis, Eimeria leucisci, Eimeria rutile, Eimeria vanasi, Eimeria amphisbaeniarum, Eimeria witchery, Eimeria yemenensae,*

*Eimeria adenoeides, Eimeria colchici, Eimeria curvata, Eimeria dispersa, Eimeria duodenalis, Eimeria fraterculae, Eimeria gallopavonis, Eimeria innocua, Eimeria meleagridis, Eimeria meleagrimitis, Eimeria phasiani, Eimeria procera, Eimeria purpureicephali, Eimeria ahsata, Eimeria alabamensis, Eimeria alijevi, Eimeria aspheronica, Eimeria arloingi, Eimeria arundeli, Eimeria bakuensis, Eimeria bovis, Eimeria cameli, Eimeria caprina, Eimeria caprovina, Eimeria christenseni, Eimeria clethrionomyis, Eimeria coecicola, Eimeria contorta, Eimeria couesii, Eimeria crandallis, Eimeria dammahensis, Eimeria dowleri, Eimeria exigua, Eimeria falciformis, Eimeria farasanii, Eimeria ferrisi, Eimeria flavescens, Eimeria gallatii, Eimeria granulosa, Eimeria hirci, Eimeria intestinalis, Eimeria irresidua, Eimeria intricata, Eimeria jolchijevi, Eimeria krijgsmanni, Eimeria larimerensis, Eimeria macusaniensis, Eimeria magna, Eimeria marconii, Eimeria media, Eimeria melanuri, Eimeria myoxi, Eimeria nagpurensis, Eimeria nieschulzi, Eimeria ninakohlyakimovae, Eimeria ovinoidalis, Eimeria pallida, Eimeria palustris, Eimeria papillata, Eimeria perforans, Eimeria phocae, Eimeria pileata, Eimeria pipistrellus, Eimeria piriformis, Eimeria prionotemni, Eimeria procyonis, Eimeria punctate, Eimeria roobroucki, Eimeria saudiensis, Eimeria sealanderi, Eimeria separata, Eimeria stiedae, Eimeria ursini, Eimeria vermiformis, Eimeria weybridgensis, Eimeria wobati*, and *Eimeria zuernii*.

The composition according to one embodiment may have an excellent effect of prevention, alleviation and/or treatment of coccidiosis caused by at least one protozoan selected from the group consisting of *Eimeria* sp. protozoa described in Table 1 below, and the *Eimeria* sp. protozoa described in Table 1 below may cause coccidiosis of animals described in Table 1, respectively.

TABLE 1

| species | Host animal |
|---|---|
| 1 *Eimeria acervulina* | Chicken (*Gallus gallus domesticus*) |
| 2 *Eimeria tenella* | Chicken (*Gallus gallus domesticus*) |
| 3 *Eimeria maxima* | Chicken (*Gallus gallus domesticus*) |
| 4 *Eimeria necatrix* | Chicken (*Gallus gallus domesticus*) |
| 5 *Eimeria brunetti* | Chicken (*Gallus gallus domesticus*) |
| 6 *Eimeria hagani* | Chicken (*Gallus gallus domesticus*) |
| 7 *Eimeria mitis* | Chicken (*Gallus gallus domesticus*) |
| 8 *Eimeria praecox* | Chicken (*Gallus gallus domesticus*) |
| 9 *Eimeria mivati* | Chicken (*Gallus gallus domesticus*) |
| 10 *Eimeria aurati* | Goldfish (*Carassius auratus*) |
| 11 *Eimeria baueri* | Carp (crucian carp (*Carassius carassius*)) |
| 12 *Eimeria lepidosirenis* | South American lungfish (*Lepidosiren paradoxa*) |
| 13 *Eimeria leucisci* | Barbel (common barbel (*Barbus barbus bocagei*)) |
| 14 *Eimeria rutile* | European chub (*Leuciscus cephalus cabeda*), Iberian nase (*Chondrostoma polylepis polylepis*) |
| 15 *Eimeria vanasi* | blue tilapia (*Oreochromis aureus*) |
| 16 *Eimeria amphisbaeniarum* | Worm lizard (Mann's worm lizard (*Amphisbaena manni*)) |
| 17 *Eimeria witchery* | Worm lizard (Mann's worm lizard (*A. manni*)) |
| 18 *Eimeria yemenensae* | Rainbow agama (rock agama (*Agama yemenensis*)) |
| 19 *Eimeria adenoeides* | Turkey (*Meleagris gallopavo*) |
| 20 *Eimeria colchici* | Pheasant (common pheasant (*Phasianus colchicus*)) |
| 21 *Eimeria curvata* | Ruddy ground dove (*Columbina talpacoti*), scaled dove (*Scardafella squammata*) |
| 22 *Eimeria dispersa* | Turkey (*M. gallopavo*), quail (bobwhite quail (*Colinus virginianus*)) |
| 23 *Eimeria duodenalis* | Pheasant (common pheasant (*Phasianus colchicus*)) |
| 24 *Eimeria fraterculae* | Atlantic puffin (*Fratercula arctica*) |
| 25 *Eimeria gallopavonis* | Turkey (*M. gallopavo*) |
| 26 *Eimeria innocua* | Turkey (*M. gallopavo*) |
| 27 *Eimeria meleagridis* | Turkey (*M. gallopavo*) |
| 28 *Eimeria meleagrimitis* | Turkey (*M. gallopavo*) |
| 29 *Eimeria phasiani* | Pheasant (*P. colchicus*) |
| 30 *Eimeria procera* | Grey partridges (*Perdix perdix*) |
| 31 *Eimeria purpureicephali* | Red-capped parrot (*Purpureicephalus spurius*) |
| 32 *Eimeria ahsata* | Goat (*Capra hircus*), sheep (*Ovis aries*) |
| 33 *Eimeria alabamensis* | Cattle (*Bos taurus*) |
| 34 *Eimeria alijevi* | Goat (*C. hircus*) |
| 35 *Eimeria aspheronica* | Goat (*C. hircus*) |
| 36 *Eimeria arloingi* | Goat (*C. hircus*) |
| 37 *Eimeria arundeli* | Common wombat (*Vombatus ursinus*) |
| 38 *Eimeria bakuensis* | Sheep (*O. aries*) |
| 39 *Eimeria bovis* | Cattle (*B. taurus*) |
| 40 *Eimeria cameli* | Camels (*Camelus bactrianus*, *Camelus dromedarius*) |
| 41 *Eimeria caprina* | Goat (*C. hircus*) |
| 42 *Eimeria caprovina* | Goat (*C. hircus*) |
| 43 *Eimeria christenseni* | Goat (*C. hircus*) |
| 44 *Eimeria clethrionomyis* | Red-backed vole (*Clethrionomys gapperi*) |
| 45 *Eimeria coecicola* | Rabbit (*Oryctolagus cuniculus*) |
| 46 *Eimeria contorta* | Mouse (*Mus musculus*) |
| 47 *Eimeria couesii* | Rice rat (*Oryzomys couesi*) |
| 48 *Eimeria crandallis* | Sheep (*O. aries*) |
| 49 *Eimeria dammahensis* | Scimitar-homed oryx (*Oryx dammah*) |
| 50 *Eimeria dowleri* | Eastern red bat (*Lasiurus borealis*) |
| 51 *Eimeria exigua* | Rabbit (*O. cuniculus*) |
| 52 *Eimeria falciformis* | Mouse (*M. musculus*) |
| 53 *Eimeria farasanii* | Mountain gazelle (*Gazella gazelle farasani*) |
| 54 *Eimeria ferrisi* | Mouse (*M. musculus*) |
| 55 *Eimeria flavescens* | Rabbit (*O. cuniculus*) |
| 56 *Eimeria gallatii* | Red-backed vole (*Clethrionomys gapperi*) |
| 57 *Eimeria granulosa* | Goat (*C. hircus*) |
| 58 *Eimeria hirci* | Goat (*C. hircus*) |
| 59 *Eimeria intestinalis* | Rabbit (*O. cuniculus*) |
| 60 *Eimeria irresidua* | Rabbit (*O. cuniculus*) |
| 61 *Eimeria intricata* | Goat (*C. hircus*) |
| 62 *Eimeria jolchijevi* | Goat (*C. hircus*) |
| 63 *Eimeria krijgsmanni* | Mouse (*M. musculus*) |
| 64 *Eimeria larimerensis* | Uinta ground squirrel (*Spermophilus armatus*) |
| 65 *Eimeria macusaniensis* | Llamas (*Lama glama*), guanacos (*Lama guanicoe*), alpacas (*Vicugna pacos*), vicunas (*Vicugna vicugna*) |
| 66 *Eimeria magna* | Rabbit (*O. cuniculus*) |
| 67 *Eimeria marconii* | Red-backed vole (*Clethrionomys gapperi*) |
| 68 *Eimeria media* | Rabbit (*O. cuniculus*) |
| 69 *Eimeria melanuri* | Garden dormouse (*Eliomys quercinus*) |
| 70 *Eimeria myoxi* | Garden dormouse (*Eliomys quercinus*) |
| 71 *Eimeria nagpurensis* | Rabbit (*O. cuniculus*) |
| 72 *Eimeria nieschulzi* | Brown rat (*R. norvegicus*) |
| 73 *Eimeria ninakohlyakimovae* | Goat (*C. hircus*) |
| 74 *Eimeria ovinoidalis* | Sheep (*O. aries*) |
| 75 *Eimeria pallida* | Goat (*C. hircus*) |
| 76 *Eimeria palustris* | Rice rat (marsh rice rat (*Oryzomys palustris*)) |
| 77 *Eimeria papillata* | Mouse (*M. musculus*) |
| 78 *Eimeria perforans* | Rabbit (*O. cuniculus*) |
| 79 *Eimeria phocae* | Sable Island harbour seals (*Phoca vitulina*) |
| 80 *Eimeria pileata* | Red-backed vole (*Clethrionomys gapperi*) |
| 81 *Eimeria pipistrellus* | Kuhl's pipistrelle (*Pipistrellus kuhlii*) |
| 82 *Eimeria piriformis* | Rabbit (*O. cuniculus*) |
| 83 *Eimeria prionotemni* | Bennett's wallaby (*Macropus rufogriseus*) |
| 84 *Eimeria procyonis* | Raccoon (*Procyon lotor*) |
| 85 *Eimeria punctate* | Goat (*C. hircus*) |
| 86 *Eimeria roobroucki* | Rabbit (*O. cuniculus*) |
| 87 *Eimeria saudiensis* | Arabian oryx (*Oryx leucoryx*) |

TABLE 1-continued

| species | Host animal |
|---|---|
| 88 *Eimeria sealanderi* | Eastern red bat (*Lasiurus borealis*) |
| 89 *Eimeria separata* | Mouse (*M. musculus*), rat (*Rattus rattus*) |
| 90 *Eimeria stiedae* | Rabbit (*O. cuniculus*) |
| 91 *Eimeria ursini* | Southern hairy nosed wombat (*Lasiorhinus latifrons*) |
| 92 *Eimeria vermiformis* | Mouse (*M. musculus*) |
| 93 *Eimeria weybridgensis* | Sheep (*O. aries*) |
| 94 *Eimeria wobati* | Southern hairy-nosed wombat (*L. latifrons*) |
| 95 *Eimeria zuernii* | Cattle (*Bos taurus*) |

The composition according to one embodiment may have an excellent effect for prevention, alleviation and/or treatment of coccidiosis caused by *Eimeria tenella, Eimeria acervulina*, and/or *Eimeria maxima.*

In one embodiment, the prevention or alleviation of coccidiosis may mean at least one (for example, any one, 2 or more kinds, 3 or more kinds, or all) selected from the group consisting of the following (1) to (4), and for example, at least one selected from the group consisting of the following (1) to (4) may be reduce, inhibited and/or increased compared to a control group (negative control group and/or positive control group):

(1) reduction of at least one selected from the group consisting of lesion score (for example, appendix lesion score), fecal oocyst excretion amount and mortality;
(2) inhibition of weight loss due to coccidiosis;
(3) increase of an anticoccidial index (ACI); and
(4) reduction of cell invasion of an *Eimeria* sp. protozoan, propagation of the protozoan in cells, or both.

In one embodiment, the lesion scoring method which determines the lesion score may be performed by referring to Johnson J K & Reid W M (1970) document (Joyce Johnson, W. Malcolm Reid, Anticoccidial drugs: Lesion scoring techniques in battery and floor-pen experiments with chickens, Experimental parasitology, 1970), and the lesion score may be 0 to 4 degrees. In one embodiment, the lesion score may mean a lesion score measured in appendix, duodenum and/or jejunum, and it may be calculated by a sum of each of lesion scores measured in each organ (appendix, duodenum and/or jejunum).

In one embodiment, the fecal oocyst extraction amount may be measured using a microscope or using a counting chamber (for example, McMaster chamber) and the like by collecting feces excreted from a subject.

In one embodiment, the mortality may mean mortality of an animal subject in which coccidiosis is induced, and by performing a post mortem, the number of subjects died from causes other than coccidiosis may be excluded.

In one embodiment, the subject in which coccidiosis is induced may have a reduced body weight than a subject in which coccidiosis is not induced, and the composition according to one embodiment may inhibit weight loss by induction of coccidiosis.

In one embodiment, the anticoccidial index may be calculated by Equation 1 below, and in Equation 1, the lesion score may be calculated as aforementioned.

Anticoccidial index (ACI)=(survival rate after challenge inoculation (%))+(daily weight gain compared to negative control group (%))−(lesion score×10)−(fecal oocyst excretion amount index) (Equation 1)

The challenge inoculation may mean administration (for example, oral inoculation, etc.) of a protozoan capable of inducing coccidiosis. In one embodiment, the survival rate may be a survival rate measured at Day 5 to 10, Day 7 to 10, Day 8 to 10, Day 7 to 9, Day 7 to 8, or Day 7 after challenge inoculation, and by performing a post mortem, the survival rate may be measured by excluding the number of subjects died from causes other than coccidiosis.

The weight gain compared to the negative control group in Equation 1 above may be a value calculated by a percentage calculated on the basis of a value of the negative control group (for example, negative control group in which a protozoan is non-infected).

The lesion score in Equation 1 above is as described above.

In Equation 1 above, the fecal oocyst excretion amount index may be a numerical value of 0 when the calculated result value is at a level of 0% or more to less than 1%, 5 when the calculated result value is at a level of 1% or more to less than 26%, 10 when the calculated result value is at a level of 26% or more to less than 51%, 20 when the calculated result value is at a level of 51% or more to less than 76% and 40 when the calculated result value is at a level of 76% or more to 100% or less, by calculating a percentage based on a value of a negative control group (for example, negative control group in which a protozoan is infected).

In one embodiment, the coumaric acid and/or salt thereof may be comprised in the feed composition by 1 w/w % or less, less than 1 w/w %, $10^{-1}$ w/w % or less, $5\times10^{-2}$ w/w % or less, $2.5\times10^{-2}$ w/w % or less, $2\times10^{-2}$ w/w % or less, $1.25\times10^{-2}$ w/w % or less, $10^{-2}$ w/w % or less, $9\times10^{-3}$ w/w % or less, $8\times10^{-3}$ w/w % or less, $7\times10^{-3}$ w/w % or less, $6\times10^{-3}$ w/w % or less, $5\times10^{-3}$ w/w % or less, $4\times10^{-3}$ w/w % or less, $10^{-7}$ w/w % or more, $10^{-6}$ w/w % or more, $10^{-5}$ w/w % or more, $10^{-4}$ w/w % or more, $5\times10^{-4}$ w/w % or more, $10^{-3}$ w/w % or more, $1.5\times10^{-3}$ w/w % or more, $2\times10^{-3}$ w/w % or more, $3\times10^{-3}$ w/w % or more, $4\times10^{-3}$ w/w % or more, $5\times10^{-3}$ w/w % or more, $10^{-7}$ to 1 w/w %, $10^{-7}$ to $10^{-1}$ w/w %, $10^{-7}$ to $5\times10^{-2}$ w/w %, $10^{-7}$ to $10^{-2}$ w/w %, $10^{-7}$ to $5\times10^{-3}$ w/w %, $10^{-7}$ to $4\times10^{-3}$ w/w %, $10^{-7}$ to $10^{-3}$ w/w %, $10^{-7}$ to $5\times10^{-4}$ w/w %, $10^{-7}$ to $10^{-4}$ w/w %, $10^{-7}$ to $10^{-5}$ w/w %, $10^{-6}$ to 1 w/w %, $10^{-6}$ to $10^{-1}$ w/w %, $10^{-6}$ to $5\times10^{-2}$ w/w %, $10^{-6}$ to $10^{-2}$ w/w %, $10^{-6}$ to $5\times10^{-3}$ w/w %, $10^{-6}$ to $4\times10^{-3}$ w/w %, $10^{-6}$ to $10^{-3}$ w/w %, $10^{-6}$ to $5\times10^{-4}$ w/w %, $10^{-6}$ to $10^{-4}$ w/w %, $10^{-6}$ to $10^{-5}$ w/w %, $10^{-5}$ to 1 w/w %, $10^{-5}$ to $10^{-1}$ w/w %, $10^{-5}$ to $5\times10^{-2}$ w/w %, $10^{-5}$ to $10^{-2}$ w/w %, $10^{-5}$ to $5\times10^{-3}$ w/w %, $10^{-5}$ to $4\times10^{-3}$ w/w %, $10^{-5}$ to $10^{-3}$ w/w %, $10^{-5}$ to $5\times10^{-4}$ w/w %, $10^{-5}$ to $10^{-4}$ w/w %, $10^{-4}$ to 1 w/w %, $10^{-4}$ to $10^{-1}$ w/w %, $10^{-4}$ to $5\times10^{-2}$ w/w %, $10^{-4}$ to $10^{-2}$ w/w %, $10^{-4}$ to $5\times10^{-3}$ w/w %, $10^{-4}$ to $4\times10^{-3}$ w/w %, 10 to $10^{-3}$ w/w %, $10^{-4}$ to $5\times10^{-4}$ w/w %, $10^{-3}$ to 1 w/w %, $10^{-3}$ to $10^{-1}$ w/w %, $10^{-3}$ to $5\times10^{-2}$ w/w %, $10^{-3}$ to $10^{-2}$ w/w %, $10^{-3}$ to $5\times10^{-3}$ w/w %, $10^{-3}$ to $4\times10^{-3}$ w/w %, $10^{-3}$ to $2\times10^{-3}$ w/w %, or $10^{-3}$ to $1.5\times10^{-3}$ w/w %. In one embodiment, the feed composition may be a feed (for example, assorted feed and/or ingredient feed finally ingested by an animal) comprising the active ingredient in the range based on the total weight.

In one embodiment, the coumaric acid and/or salt thereof may be comprised in the feed composition at a concentration of 1000 ppm or less, 500 ppm or less, 400 ppm or less, 300 ppm or less, 250 ppm or less, 200 ppm or less, 125 ppm or less, less than 125 ppm, 100 ppm or less, 90 ppm or less, 80 ppm or less, 70 ppm or less, 65 ppm or less, 62.5 ppm or less, 60 ppm or less, 50 ppm or less, 0.1 ppm or more, 1 ppm or more, 5 ppm or more, 10 ppm or more, 15 ppm or more, 20 ppm or more, 30 ppm or more, 40 ppm or more, 50 ppm or more, 62.5 ppm or more, 0.1 to 1000 ppm, 0.1 to 500 ppm, 0.1 to 400 ppm, 0.1 to 300 ppm, 0.1 to 250 ppm, 0.1 to 200 ppm, 0.1 to 125 ppm, 0.1 to 100 ppm, 0.1 to 90 ppm, 0.1 to 80 ppm, 0.1 to 70 ppm, 0.1 to 65 ppm, 0.1 to 60 ppm, 0.1 to 50 ppm, 1 to 1000 ppm, 1 to 500 ppm, 1 to 400 ppm, 1 to 300 ppm, 1 to 250 ppm, 1 to 200 ppm, 1 to 125 ppm, 1 to 100 ppm, 1 to 90 ppm, 1 to 80 ppm, 1 to 70 ppm, 1 to 65 ppm, 1 to 60 ppm, 1 to 50 ppm, 5 to 1000 ppm, 5 to 500 ppm, 5 to 400 ppm, 5 to 300 ppm, 5 to 250 ppm, 5 to 200 ppm, 5 to 125 ppm, 5 to 100 ppm, 5 to 90 ppm, 5 to 80 ppm, 5 to 70 ppm, 5 to 65 ppm, 5 to 60 ppm, 5 to 50 ppm, 10 to 1000 ppm, 10 to 500 ppm, 10 to 400 ppm, 10 to 300 ppm, 10 to 250 ppm, 10 to 200 ppm, 10 to 125 ppm, 10 to 100 ppm, 10 to 90 ppm, 10 to 80 ppm, 10 to 70 ppm, 10 to 65 ppm, 10 to 60 ppm, 10 to 50 ppm, 20 to 1000 ppm, 20 to 500 ppm, 20 to 400 ppm, 20 to 300 ppm, 20 to 250 ppm, 20 to 200 ppm, 20 to 125 ppm, 20 to 100 ppm, 20 to 90 ppm, 20 to 80 ppm, 20 to 70 ppm, 20 to 65 ppm, 20 to 60 ppm, 20 to 50 ppm, 30 to 1000 ppm, 30 to 500 ppm, 30 to 400 ppm, 30 to 300 ppm, 30 to 250 ppm, 30 to 200 ppm, 30 to 125 ppm, 30 to 100 ppm, 30 to 90 ppm, 30 to 80 ppm, 30 to 70 ppm, 30 to 65 ppm, 30 to 60 ppm, 30 to 50 ppm, 40 to 1000 ppm, 40 to 500 ppm, 40 to 400 ppm, 40 to 300 ppm, 40 to 250 ppm, 40 to 200 ppm, 40 to 125 ppm, 40 to 100 ppm, 40 to 90 ppm, 40 to 80 ppm, 40 to 70 ppm, 40 to 65 ppm, 40 to 60 ppm, 40 to 50 ppm, 50 to 1000 ppm, 50 to 500 ppm, 50 to 400 ppm, 50 to 300 ppm, 50 to 250 ppm, 50 to 200 ppm, 50 to 125 ppm, 50 to 100 ppm, 50 to 90 ppm, 50 to 80 ppm, 50 to 70 ppm, 50 to 65 ppm, or 50 to 60 ppm.

In the present application, "feed" may mean any natural or artificial diet, one-meal meal or the like for an animal to eat, ingest and digest or suitable therefor or a component of the one-meal meal. In the feed composition according to one embodiment, a concentrated feed and/or a special feed may be further comprised. The concentrated feed is a by-product obtained by purifying seed fruits and grains including grains such as wheat, oats, corn and the like, and may be bran including rice bran, wheat bran, barley bran and the like, sesame cake which is a by-product obtained by drilling soy beans, fluid, sesame seeds, flax seeds, coco palms, and the like for oil, and residues such as residual starch, which is a main component of starch residue that is the remainder after removing starch from sweet potatoes and potatoes, fish soluble obtained by concentrating fresh liquid (液狀物) obtained from fish meal, fish waste and fish, animal feed such as dried whey in which whey that is the remainder when casein is produced from meat meal (肉粉), blood meal, feather meal, skim milk powder, milk to cheese, skim milk, and the like, yeast, chlorella and/or seaweed, and the like.

The feed composition according to one embodiment may mean a feed in a form which is finally ingested by an animal, a dietary supplement capable of being mixed to feed, and/or a feed additive. The dietary supplement is for example, a composition containing a preparation which provides a therapeutic agent or a digestive agent to an animal, and may mean a composition which is not a common source of calorie intake of a living body, that is, an energy source, but is ingested in addition to a normal animal feed. The feed additive refers to a substance added to feed for a purpose of various effects such as nutrient supplementation and weight loss prevention, improvement of digestibility of fiber in feed, oil quality improvement, reproductive disorder prevention and fertility rate enhancement, prevention of high temperature stress in summer and the like. In one embodiment, it may mean a substance which is added for a purpose of prevention, alleviation or treatment of coccidiosis.

In one embodiment, the feed composition may be a feed additive, and when the feed additive according to one embodiment is mixed to feed (for example, mixed feed and/or ingredient feed finally ingested to an animal), it may be added in a weight of 0.001% or more, 0.005% or more, 0.01% or more, 0.05% or more, 0.1% or more, 0.5% or more, 1% or less, 0.5% or less, 0.1% or less, 0.05% or less, 0.01% or less, 0.005% or less, 0.001 to 1%, 0.001 to 0.5%, 0.001 to 0.1%, 0.001 to 0.05%, 0.001 to 0.01%, 0.001 to 0.005%, 0.005 to 1%, 0.005 to 0.5%, 0.005 to 0.1%, 0.005 to 0.05%, 0.005 to 0.01%, 0.01 to 1%, 0.01 to 0.5%, 0.01 to 0.1%, 0.01 to 0.05%, 0.05 to 1%, 0.05 to 0.5%, 0.05 to 0.1%, 0.1 to 1%, 0.1 to 0.5%, or 0.5 to 1% based on the total feed weight, and it may be mixed with feed raw materials, supplementary feed, adjuvants and/or other kinds of additives and the like other than the active ingredient according to one embodiment.

One aspect may provide a pharmaceutical composition for preventing or treating coccidiosis, comprising a coumaric acid and/or salt thereof, and the coumaric acid and/or salt thereof comprised in a pharmaceutical composition is as described above.

The pharmaceutical composition according to one embodiment may be used as a single formulation, and may be used by preparing a mixed formulation by further comprising an authorized pharmaceutical composition known to have an effect of preventing or treating coccidiosis. It may be formulated into a pharmaceutical unit administration form by adding a pharmaceutically acceptable carrier, excipient or diluent.

In the present application, "pharmaceutically acceptable" means that it does not significantly stimulate an organism and does not inhibit the biological activity and properties of an administration active substance. The pharmaceutical composition comprising the pharmaceutically acceptable carrier according to one embodiment may have any one formulation selected from the group consisting of a tablet, pill, powder, a granule, a capsule, suspension, internal solution, emulsion, syrup, sterilized aqueous solution, non-aqueous solution, suspension, emulsion, a freeze-dried formulation and a suppository.

The pharmaceutical composition may be various oral or parenteral formulations. In case of formulation, it may be prepared using a commonly used filler, extender, binder, wetting agent, disintegrant, diluent such as a surfactant, or excipient.

Solid preparations for oral administration include tablets, pills, powder, granules, capsules and the like, and these solid preparations may be prepared by mixing at least one excipient, for example, starch, calcium carbonate, sucrose or lactose, gelatin and the like to one or more compounds. In addition, other than simple excipients, lubricants such as magnesium stearate, talc and the like may be used. Liquid preparations for oral administration include suspension, internal solution, emulsion, syrup and the like, and various excipients, for example, wetting agents, sweeteners, fragrances, preservatives and the like other than water and liquid paraffin which are commonly used simple diluents may be comprised.

Preparations for parenteral administration may include sterilized aqueous solution, non-aqueous solution, suspension, emulsion, a freeze-dried formulation and a suppository. As the non-aqueous solution and suspension, propylene glycol, polyethylene glycol, vegetable oil such as olive oil, injectable ester such as ethyl oleate, and the like may be used. As a base of the suppository, witepsol macrogol, tween 61, cacao butter, laurin butter, glycerogelatin and the like may be used.

In one embodiment, the pharmaceutical composition may be used by formulation into various forms such as oral formulations such as powder, granules, tablets, capsules, suspension, emulsion, syrup, aerosols, and the like, injectable formulations of sterilized injection solutions, and the like according to a common method for each purpose of use, and it may be orally administered or administered through various routes including intravenous, intraperitoneal, subcutaneous, intra-rectal, topical administration and the like.

In one embodiment, a carrier, excipient or diluent or the like may be further comprised in the pharmaceutical composition additionally, and the example of the suitable carrier, excipient or diluent which may be comprised may include lactose, dextrose, sucrose, sorbitol, mannitol, xylitol, erythritol, maltitol, starch, acacia gum, alginate, gelatin, calcium phosphate, calcium silicate, cellulose, methyl cellulose, amorphous cellulose, polyvinyl pyrrolidone, water, methylhydroxybenzoate, propylhydroxy benzoate, talc, magnesium stearate and mineral oil and the like. In addition, the pharmaceutical composition may further comprise a filler, anticoagulant, lubricant, wetting agent, flavoring, emulsifier, preservative or the like additionally.

In one embodiment, the effective amount of the coumaric acid and/or salt thereof in the pharmaceutical composition may differ depending on the patient (subject)'s age, gender and body weight, and in general, 0.0001 to 0.001 mg/kg, 0.0001 to 0.01 mg/kg, 0.0001 to 0.1 mg/kg, 0.0001 to 1 mg/kg, 0.0001 to 10 mg/kg, 0.0001 to 100 mg/kg, 0.0001 to 231 mg/kg, 0.0001 to 250 mg/kg, 0.0001 to 500 mg/kg, 0.0001 to 1000 mg/kg, 0.001 to 0.01 mg/kg, 0.001 to 0.1 mg/kg, 0.001 to 1 mg/kg, 0.001 to 10 mg/kg, 0.001 to 100 mg/kg, 0.001 to 231 mg/kg, 0.001 to 250 mg/kg, 0.001 to 500 mg/kg, 0.001 to 1000 mg/kg, 0.01 to 0.1 mg/kg, 0.01 to 1 mg/kg, 0.01 to 10 mg/kg, 0.01 to 100 mg/kg, 0.01 to 250 mg/kg, 0.01 to 500 mg/kg, 0.01 to 1000 mg/kg, 0.1 to 1 mg/kg, 0.1 to 10 mg/kg, 0.1 to 100 mg/kg, 0.1 to 231 mg/kg, 0.1 to 250 mg/kg, 0.1 to 500 mg/kg, 0.1 to 1000 mg/kg, 1 to 10 mg/kg, 1 to 100 mg/kg, 1 to 231 mg/kg, 1 to 250 mg/kg, 1 to 500 mg/kg, 1 to 1000 mg/kg, 10 to 100 mg/kg, 10 to 231 mg/kg, 10 to 250 mg/kg, 10 to 500 mg/kg, 10 to 1000 mg/kg, 100 to 231 mg/kg, 100 to 250 mg/kg, 100 to 500 mg/kg, 100 to 1000 mg/kg, 250 to 500 mg/kg, or 250 to 1000 mg/kg per body weight kg may be administered daily or on alternate days or be administered by dividing into 1 to 3 times per day. However, since it may be increased or decreased according to the administration route, severity of disease, gender, body weight, age and the like, the dosage does not limit the scope of the present application in any way. In one embodiment, when the composition is administered intraperitoneally, it may be administered at a concentration of 0.001 to 250 mg/kg or 0.001 to 231 mg/kg.

In one embodiment, the dosage of the pharmaceutical composition may be in various ranges depending on the patient's body weight, age, gender, health status, diet, administration time, administration method, excretion rate and severity of disease and the like.

In one embodiment, the coumaric acid and/or salt thereof may be comprised in the pharmaceutical composition by 1 w/w % or less, less than 1 w/w %, $10^{-1}$ w/w % or less, $5\times10^{-2}$ w/w % or less, $2.5\times10^{-2}$ w/w % or less, $2\times10^{-2}$ w/w % or less, $1.25\times10^{-2}$ w/w % or less, $10^{-2}$ w/w % or less, $9\times10^{-3}$ w/w % or less, $8\times10^{-3}$ w/w % or less, $7\times10^{-3}$ w/w % or less, $6\times10^{-3}$ w/w % or less, $5\times10^{-3}$ w/w % or less, $4\times10^{-3}$ w/w % or less, $10^{-7}$ w/w % or more, $10^{-6}$ w/w % or more, $10^{-5}$ w/w % or more, $10^{-4}$ w/w % or more, $5\times10^{-4}$ w/w % or more, $10^{-3}$ w/w % or more, $1.5\times10^{-3}$ w/w % or more, $2\times10^{-3}$ w/w % or more, $3\times10^{-3}$ w/w % or more, $4\times10^{-3}$ w/w % or more, $5\times10^{-3}$ w/w % or more, $10^{-7}$ to 1 w/w %, $10^{-7}$ to $10^{-1}$ w/w %, $10^{-7}$ to $5\times10^{-2}$ w/w %, $10^{-7}$ to $10^{-2}$ w/w %, $10^{-7}$ to $5\times10^{-3}$ w/w %, $10^{-7}$ to $4\times10^{-3}$ w/w %, $10^{-7}$ to $10^{-3}$ w/w %, $10^{-7}$ to $5\times10^{-4}$ w/w %, $10^{-7}$ to $10^{-4}$ w/w %, $10^{-7}$ to $10^{-5}$ w/w %, $10^{-6}$ to 1 w/w %, $10^{-6}$ to $10^{-1}$ w/w %, $10^{-6}$ to $5\times10^{-2}$ w/w %, $10^{-6}$ to $10^{-2}$ w/w %, $10^{-6}$ to $5\times10^{-3}$ w/w %, $10^{-6}$ to $4\times10^{-3}$ w/w %, $10^{-6}$ to $10^{-3}$ w/w %, $10^{-6}$ to $5\times10^{-4}$ w/w %, $10^{-6}$ to $10^{-4}$ w/w %, $10^{-6}$ to $10^{-5}$ w/w %, $10^{-5}$ to 1 w/w %, $10^{-5}$ to $10^{-1}$ w/w %, $10^{-5}$ to $5\times10^{-2}$ w/w %, $10^{-5}$ to $10^{-2}$ w/w %, $10^{-5}$ to $5\times10^{-3}$ w/w %, $10^{-5}$ to $4\times10^{-3}$ w/w %, $10^{-5}$ to $10^{-3}$ w/w %, $10^{-5}$ to $5\times10^{-4}$ w/w %, $10^{-5}$ to $10^{-4}$ w/w %, $10^{-4}$ to 1 w/w %, $10^{-4}$ to $10^{-1}$ w/w %, $10^{-4}$ to $5\times10^{-2}$ w/w %, $10^{-4}$ to $10^{-2}$ w/w %, $10^{-4}$ to $5\times10^{-3}$ w/w %, $10^{-4}$ to $4\times10^{-3}$ w/w %, $10^{-4}$ to $10^{-3}$ w/w %, $10^{-4}$ to $5\times10^{-4}$ w/w %, $10^{-3}$ to 1 w/w %, $10^{-3}$ to $10^{-1}$ w/w %, $10^{-3}$ to $5\times10^{-2}$ w/w %, $10^{-3}$ to $10^{-2}$ w/w %, $10^{-3}$ to $5\times10^{-3}$ w/w %, $10^{-3}$ to $4\times10^{-3}$ w/w %, $10^{-3}$ to $2\times10^{-3}$ w/w %, or $10^{-3}$ to $1.5\times10^{-3}$ w/w.

In one embodiment, the coumaric acid and/or salt thereof may be comprised in the pharmaceutical composition at a concentration of 1000 ppm or less, 500 ppm or less, 400 ppm or less, 300 ppm or less, 250 ppm or less, 200 ppm or less, 125 ppm or less, less than 125 ppm, 100 ppm or less, 90 ppm or less, 80 ppm or less, 70 ppm or less, 65 ppm or less, 60 ppm or less, 62.5 ppm or less, 50 ppm or less, 0.1 ppm or more, 1 ppm or more, 5 ppm or more, 10 ppm or more, 15 ppm or more, 20 ppm or more, 30 ppm or more, 40 ppm or more, 50 ppm or more, 62.5 ppm or more, 0.1 to 1000 ppm, 0.1 to 500 ppm, 0.1 to 400 ppm, 0.1 to 300 ppm, 0.1 to 250 ppm, 0.1 to 200 ppm, 0.1 to 125 ppm, 0.1 to 100 ppm, 0.1 to 90 ppm, 0.1 to 80 ppm, 0.1 to 70 ppm, 0.1 to 65 ppm, 0.1 to 60 ppm, 0.1 to 50 ppm, 1 to 1000 ppm, 1 to 500 ppm, 1 to 400 ppm, 1 to 300 ppm, 1 to 250 ppm, 1 to 200 ppm, 1 to 125 ppm, 1 to 100 ppm, 1 to 90 ppm, 1 to 80 ppm, 1 to 70 ppm, 1 to 65 ppm, 1 to 60 ppm, 1 to 50 ppm, 5 to 1000 ppm, 5 to 500 ppm, 5 to 400 ppm, 5 to 300 ppm, 5 to 250 ppm, 5 to 200 ppm, 5 to 125 ppm, 5 to 100 ppm, 5 to 90 ppm, 5 to 80 ppm, 5 to 70 ppm, 5 to 65 ppm, 5 to 60 ppm, 5 to 50 ppm, 10 to 1000 ppm, 10 to 500 ppm, 10 to 400 ppm, 10 to 300 ppm, 10 to 250 ppm, 10 to 200 ppm, 10 to 125 ppm, 10 to 100 ppm, 10 to 90 ppm, 10 to 80 ppm, 10 to 70 ppm, 10 to 65 ppm, 10 to 60 ppm, 10 to 50 ppm, 20 to 1000 ppm, 20 to 500 ppm, 20 to 400 ppm, 20 to 300 ppm, 20 to 250 ppm, 20 to 200 ppm, 20 to 125 ppm, 20 to 100 ppm, 20 to 90 ppm, 20 to 80 ppm, 20 to 70 ppm, 20 to 65 ppm, 20 to 60 ppm, 20 to 50 ppm, 30 to 1000 ppm, 30 to 500 ppm, 30 to 400 ppm, 30 to 300 ppm, 30 to 250 ppm, 30 to 200 ppm, 30 to 125 ppm, 30 to 100 ppm, 30 to 90 ppm, 30 to 80 ppm, 30 to 70 ppm, 30 to 65 ppm, 30 to 60 ppm, 30 to 50 ppm, 40 to 1000 ppm, 40 to 500 ppm, 40 to 400 ppm, 40 to 300 ppm, 40 to 250 ppm, 40 to 200 ppm, 40 to 125 ppm, 40 to 100 ppm, 40 to 90 ppm, 40 to 80 ppm, 40 to 70 ppm, 40 to 65 ppm, 40 to 60 ppm, 40 to 50 ppm, 50 to 1000 ppm, 50 to 500 ppm, 50 to 400 ppm, 50 to 300 ppm, 50 to 250 ppm, 50 to 200 ppm, 50 to 125 ppm, 50 to 100 ppm, 50 to 90 ppm, 50 to 80 ppm, 50 to 70 ppm, 50 to 65 ppm, or 50 to 60 ppm.

In one embodiment, the pharmaceutical composition may be administered to a subject through various routes. The administration may mean providing a certain substance into a subject (patient) by any appropriate method, and the administration route of the pharmaceutical composition may be oral administration and/or parenteral administration through all common routes as long as to reach a target tissue. In case of parenteral administration, external application for skin, intraperitoneal injection, intra-rectal injection, subcutaneous injection, intravenous injection, intramuscular injection and/or intrathoracic injection may be selected. In addition, the composition according to one embodiment may be administered using any device capable of delivering the active ingredient into a target cell.

Other aspect may provide an antiprotozoal composition against an *Eimeria* sp. protozoan, comprising coumaric acid and/or a salt thereof. Other aspect provides a method for preventing, alleviating and/or treating coccidiosis, or a pest control method of an *Eimeria* sp. protozoan, comprising administering coumaric acid and/or a salt thereof to an animal (for example, subject in need of protozoal pest control, or animal except for humans). In the present description, the protozoal pest control means the antiprotozoal action inclusively, and for example, it may mean the *Eimeria* sp. protozoa killing; and/or cell invasion and/or propagation inhibition of *Eimeria* sp. protozoa, and the like, but not limited thereto. Matters for the coumaric acid, salt of coumaric acid and/or *Eimeria* sp. protozoa are as described above.

In one embodiment, that the antiprotozoal activity (effect, efficacy) against an *Eimeria* sp. protozoan is excellent may mean the following characteristics of (1) and/or (2), and for example, it may exhibit the following characteristics of (1) and/or (2) compared to a control group (negative control group and/or positive control group):

(1) Excellent effect of killing an *Eimeria* sp. protozoan; and/or (2) inhibition of a cell invasion effect of an *Eimeria* sp. protozoan and/or a propagation effect of the protozoan in cells.

In one embodiment, the coumaric acid and/or salt thereof may be comprised in the antiprotozoal composition in the aforementioned concentration range in the feed composition and/or pharmaceutical composition. In one embodiment, the composition comprising the active ingredient within the aforementioned concentration range may have the excellent antiprotozoal activity compared to a case of comprising it in a range other than the concentration range.

Other aspect may provide a method for preventing, alleviating or treating coccidiosis, comprising a step of administering the composition (for example, the feed composition, the feed additive, the pharmaceutical composition and/or the antiprotozoal composition) to an animal. In one embodiment, before the administering the composition, confirming (selecting) a subject (patient) in need of preventing, alleviating or treating of coccidiosis may be further comprised. The composition and coccidiosis are as described above. According to one embodiment, the confirming a subject may comprise detecting an oocyst of a protozoan capable of inducing coccidium from feces separated from a subject. In the method for preventing, alleviating or treating coccidiosis according to one embodiment, the administration method, administration route and/or dosage of the composition are as described above.

According to one embodiment, the composition may be administered in a pharmaceutically effective dose. In the present application, 'pharmaceutically effective dose' means an amount sufficient for treating disease at a reasonable benefit/danger ratio applicable to medical treatment, and the effective dose level may be determined according to the patient's disease type, severity, drug activity, sensitivity to a drug, administration time, administration route and excretion ratio, treatment period, an element comprising a drug used simultaneously and other elements well known in the medical field. According to one embodiment, the composition may be administered as an individual therapeutic agent or be administered in combination with other anticoccidial agents, and may be administered simultaneously, separately or sequentially with a conventional therapeutic agent, and may be administered single or multiple. Taking all of the elements into consideration, it is important to administer an amount that can obtain the maximum effect with a minimum amount without side effects, and this may be easily determined by those skilled in the art.

In one embodiment, the subject to which the method for preventing, alleviating or treating coccidiosis is applied means an animal in which coccidiosis is developed or may be developed, and the animal may be mammals including humans, horses, cattle, mice, rats, dogs, cats and the like, birds including poultry (for example, breeders, broilers and/or laying hens, etc.) and the like, fish, amphibians, and/or reptiles, and the like.

In one embodiment, the animal to which the method for preventing, alleviating or treating coccidiosis is applied may be at least one (for example, 1 kind or more, 2 kinds or more, or 3 kinds or more) selected from the group consisting of the animals described in Table 1 above, and for example, it may be at least one (for example, 1 kind or more, 2 kinds or more, or 3 kinds or more) selected from the group consisting of humans, chickens, ducks, geese, turkeys, quails, pheasants, pigeons, parrots, cattle, pigs, goats, sheep, horses, antelopes, oryxes, monkeys, cats, dogs, mice, rats, rabbits, racoons, squirrels, bats, guinea pigs, camels, llamas, alpaca, wombats, lizards, goldfish, crucian carp, tilapias, barbells, lungfish and European chubs. In one embodiment, the animal may be an animal except for human.

Advantageous Effects

The composition comprising coumaric acid and/or a salt thereof according to one embodiment has excellent cell invasion inhibitory effect of the protozoa capable of inducing coccidiosis, and/or propagation inhibitory effect of the protozoa in cells, and has excellent effects of preventing, alleviating and treating coccidiosis in vivo, and significantly reduces the fecal oocyst excretion rate, so it can lower secondary coccidiosis infection.

BRIEF DESCRIPTION OF THE DRAWINGS

FIG. 1 shows the anticoccidial index (ACI) of coumaric acid when protozoa capable of causing coccidiosis are inoculated.

MODE FOR INVENTION

Hereinafter, the present invention will be described in more detail by the following examples. However, they are intended to illustrate the present invention only, but the scope of the present invention is not limited by these examples.

Example 1. In Vivo Anticoccidial Activity of Coumaric Acid

Example 1-1. Experimental Facility and Research Design

An in vivo efficacy evaluation test was performed in an exclusive broiler animal experiment facility in U.S. One-day-old female Ross broilers were individually weighed and randomly divided into groups to use in an experiment.

Matters and conditions for experimental design were described in Table 2.

TABLE 2

| Category | Experiment variable |
|---|---|
| Breeding type | Cage |
| Broiler stocking age | 1-day-old |
| Total experiment period | 30 days |
| Gender | Female |
| Number of broilers per cage | 6 |
| Number of repetitions per treatment group | 3 repetitions |
| Number of treatment groups | 5 |
| Total number of broilers | 90 broilers |
| Kind of challenge inoculation protozoa | *Eimeria tenella* |
| Number of challenge inoculation oocysts | 10,000 oocysts oral inoculation/broiler |

Example 1-2. Experimental Design

For the feed, Korea Feed A1-choi product was used, and each material (salinomycin (Cheil Bio Cheilsalino-60 product), VantiPEAL (Kemin, Cozante, key substance: Gallic acid), p-coumaric acid (CAS No. 501-98-4; sigma)) was added to the feed, respectively, at a concentration described in Table 3 below to be self-mixed. Antibiotics and supplements were not used in general feed and mixed feed, and no anticoccidial agent other than each material was added. Broilers were fed ad libitum throughout the experiment period.

Coccidiosis induction was performed by oral inoculation (challenge inoculation) in an oral tube type of 10,000 oocysts with over 90% mature (sporulation) *Eimeria tenella* per one individual to 14-day-old broilers.

The feed formulation administered to the control group (negative control group or positive control group) and test group and whether coccidiosis was induced by *Eimeria tenella* were described in Table 3 below. 6 1-day-old broilers were put in a cage randomly arranged for each test group, and after 14 days of feeding the general feed, the formulated feed prepared above was divided into each control group or test group and ingested.

TABLE 3

| Group | Treatment |
|---|---|
| Non-infected negative control group | General feed |
| Infected negative control group | *Eimeria tenella* infection + general feed |
| Positive control group 1 | *Eimeria tenella* infection + formulated feed comprising salinomycin 60 ppm |
| Positive control group 2 | *Eimeria tenella* infection + formulated feed comprising VantiPEAL (Kemin) 125 ppm |
| Coumaric acid treated group 1 | *Eimeria tenella* infection + formulated feed comprising p-coumaric acid (sigma) 125 ppm |

Example 1-3. Measurement of Anticoccidial Activity of Coumaric Acid

The anticoccidial efficacy by test group designed in Example 1-2 above was shown as an anticoccidial index (ACI), and the anticoccidial index was calculated by Equation 2 below. The ACI score is out of 200 points, and the higher the ACI score, the more excellent the anticoccidial ability, and when it is 120 points or more to less than 140 points, it is determined that it is effective as an anticoccidial material, and when it is 140 points or more to less than 160 points, it is determined that it is excellent as an anticoccidial material, and when it is 160 points or more, it is determined that the anticoccidial effect is very excellent. (Luis Miguel De Pablos et al., Anticoccidial activity of maslinic acid against infection with *Eimeria tenella* in chickens, Parasitol Res, 2010)

Anticoccidial index (ACI)=(survival rate after challenge inoculation (%))+(daily weight gain compared to negative control group (RWG, %))−(lesion score×10)−(fecal oocyst excretion amount index) (Equation 2)

1) Survival rate: the number of dead individuals was recorded daily, and post mortem autopsy was performed to determine a cause of mortality, and the number of individuals who died due to causes other than coccidiosis was excluded. The survival rate (%) up to the 8th day after challenge inoculation was used for anticoccidial index calculation.

2) Daily weight gain: body weight was measured for each cage before challenge inoculation with a protozoan into an individual and at the 7th day after challenge inoculation, and the difference was divided by the number of days to calculate the daily weight gain (ADG, g/d). 'Daily weight gain compared to the negative control group (RWG, %)' which was calculated by dividing the daily weight gain (ADG, average daily gain: g/d) of each experimental group by the weight gain (ADG, g/d) of the non-infected negative control group and multiplying by 100 was used for anticoccidial index calculation.

The daily weight gain (ADG, g/d) measured in each control group and test group and the daily weight gain compared to the negative control group (RWG, %) were shown in Table 4 below.

3) Lesion scoring: On the 9th day after challenge inoculation, an autopsy was conducted for 4 broilers per cage, and the intestines were incised and opened. Scoring was performed for each coccidial lesion in the appendix region of the broilers. The lesion scoring method was performed by referring to Johnson J K & Reid W M (1970) document (Joyce Johnson, W. Malcolm Reid, Anticoccidial drugs: Lesion scoring techniques in battery and floor-pen experiments with chickens, Experimental parasitology, 1970). The lesion score is on a scale of 0-4, and 0 point corresponds to normal appendix, and 1 point is a mild infection symptom, and 2 points is a moderate infection symptom, and 3 points is a severe infection symptom and 4 points is a case of showing a very severe infection symptom or causing death. The appendix lesion score measured in each control group and test group was described in Table 4 below. The measured appendix lesion score was used for calculation of the anticoccidial index by multiplying by 10.

4) Fecal oocyst excretion amount: the entire feces on the 6~9th day of challenge inoculation were collected by cage, mixed evenly, and then randomly sampled 3 times in total by 1 g each. After floating the oocysts in 1 g feces using salt water, the oocyst excretion amount was measured using McMaster chamber, and the result was described in Table 4 below.

The oocyst excretion amount (%) compared to the infected negative control group was calculated by dividing the oocyst excretion amount by each group into the oocyst excretion amount of the infected negative control group and multiplying by 100. The oocyst excretion amount index was calculated as 0 when the calculated oocyst excretion amount compared to the infected negative control group was at a level of 0% to less than 1%, 5 when it was 1% or more to less than 26%, 10 when it was 26% or more to less than 51%, 20 when it was 51% or more to less than 76%, and 40 when it was 76% or more to 100% or less, and this was used for anticoccidial index calculation.

TABLE 4

| | Group | | | | |
|---|---|---|---|---|---|
| | Control group | | | | Test group |
| | Compounds | | | | |
| | NC | PC | Salinomycin | VantiPEARL | p-coumaric acid |
| conc(ppm) | | | 60 | 125 | 125 |
| Number of broilers | 18 | 18 | 18 | 18 | 18 |
| ADG after challenge inoculation (g/d) | 55 | 37 | 45 | 49 | 52 |
| RWG(%) | 100 | 67.3 | 81.8 | 89.1 | 94.5 |
| Survival rate (%) | 100 | 100 | 100 | 100 | 100 |
| Appendix lesion score | 0 | 3.37 | 2.27 | 2.17 | 2.5 |
| Appendix lesion index | — | 33.7 | 22.7 | 21.7 | 25 |
| Oocyst excretion amount (Oocyst/chicken) | 0 | $1.3 \times 10^8$ | $6.3 \times 10^7$ | $8 \times 10^7$ | $5.7 \times 10^7$ |
| Oocyst index | 0 | 40 | 10 | 20 | 10 |
| ACI | 200 | 94 | 149 | 147 | 160 |

As shown in Table 4, in the negative control group infected by *Eimeria tenella* (PC), compared to the non-infected negative control group (NC), coccidiosis was caused, so the weight gain was reduced, and the lesion score and oocyst excretion amount were increased. The salinomycin administration group used as an anticoccidial control group, compared to the infected negative control group (PC), the weight gain was increased, and the lesion score and oocyst excretion amount were reduced. In the natural anticoccidial agent control group, VantiPEARL administration group, compared to the PC group, the weight gain was increased, and the oocyst excretion amount and lesion index were reduced.

In the p-coumaric acid administration group, compared to the PC group, the weight gain was increased, and the lesion score and oocyst excretion amount were reduced. As the result of calculating and comparing the anticoccidial index, in the p-coumaric acid 125 ppm administration group, it was 160 points, so it had excellent anticoccidial efficacy compared to the Salinomycin (149 points) and VantiPEAL (147 points) administration groups.

Example 3. Cell Invasion and Intracellular Propagation Inhibitory Effect Against *Eimeria* Protozoa of Coumaric Acid In the present example, using MDBK cell line which is a representative animal cell known to cause *Eimeria* infection and propagation, the inhibition ability of intracellular protozoan invasion and intracellular protozoal propagation of the coumaric acid was investigated.

Example 3-1. Protozoa Acquisition

A certain amount of oocysts of each of *Eimeria tenella* and *Eimeria acervulina* was put in a tube containing glass beads and pulverized, and then to remove the crushed oocyst cell wall and other debris, internal sporocysts were purified using the percoll density gradient, and washed with PBS solution. A reagent comprising sodium taurocholic acid (Sigma aldrich, USA) and trypsin (Gibco, USA), respectively, was treated to sporocysts of *Eimeria tenella, Eimeria acervulina* and *Eimeria maxima* for excystation and they were incubated, and then they were washed with PBS solution once and protozoa were obtained.

Example 3-2. Cell Invasion Inhibitory Effect of Protozoan and Intracellular Propagation Inhibitory Effect According to Coumaric Acid Treatment The protozoa of *Eimeria tenella* and *Eimeria acervulina* were obtained by the method of Example 3-1 above. Sporozoites of $2 \times 10^5$ per well were added to a well in which MDBK cells (purchased from ATCC) spread as a monolayer and each material (p-coumaric acid: sigma, CAS No. 501-98-4, and anticoccidial agents, gallic acid: sigma, CAS No. 149-91-7, salinomycin: CAS No. sigma, 53003-10-4, diclazuril: sigma, CAS No. 101831-37-2, p-coumaric acid, gallic acid and salinomycin were treated by 10 ppm, and diclazuril was treated by 1 ppm) was treated to the cells, and cultured at a temperature of 40° C. for 24 hours. The negative control group is MDBK cells infected by the protozoa, and the positive control group means a group in which gallic acid, salinomycin or diclazuril solution was incubated with the protozoa. Thereafter, in order to remove the protozoa that did not invade cells, the cells were washed twice using PBS solution. After removing the cells and protozoa inside the cells through pipetting, DNA was extracted from the cells, and PCR was performed using *E. tenella* ITS-1 (Internal transcribed spacer-1) gene or *E. acervulina* ACE gene-specific primers. The sequences of the used primers were described in Table 5 below.

TABLE 5

| Primer | | Nucleotide sequence (5'-> 3') | SEQ ID NO |
|---|---|---|---|
| *E. tenella* ITS-1 | Forward | TGGAGGGGATTATGAGAGGA | SEQ ID NO: 1 |
| | Reverse | CAAGCAGCATGTAACGGAGA | SEQ ID NO: 2 |
| *E. acervulina* ACE | Forward | GCAGTCCGATGAAAGGTATTTG | SEQ ID NO: 3 |
| | Reverse | GAAGCGAAATGTTAGGCCATCT | SEQ ID NO: 4 |

Ct values before/after washing for each material were compared and corrected with the ΔCt value of the negative control group to calculate the fold change ($2^{-\Delta Ct}$) at each time point compared to the control group, and the invasion inhibition rate (%) of the protozoa by material treatment was calculated, and the result was shown in Table 6 and Table 7. Table 6 showed the result for *Eimeria tenella*, and Table 7 showed the result for *Eimeria acervulina*.

TABLE 6

| sample | Invasion inhibition % | Propagation inhibition % |
|---|---|---|
| NC | 0.0 | 0.0 |
| Diclazuril | 6.3 | 52.9 |
| Salinomycin | 56.4 | 34.8 |
| Gallic acid | 90.1 | 0.0 |
| p-coumaric acid | 54.3 | 43.9 |

TABLE 7

| sample | Invasion inhibition % |
|---|---|
| NC | 0.0 |
| Diclazuril | 42.7 |
| Salinomycin | 59.4 |
| Gallic acid | 60.6 |
| p-coumaric acid | 82.6 |

The protozoa of *Eimeria tenella* were obtained by the method of Example 3-1 above. Sporozoites of $2\times10^5$ per well were added to a well in which MDBK cells (purchased from ATCC) spread as a monolayer and cultured at a temperature of 40° C. for 24 hours, and then, in order to remove the protozoa that did not invade cells, the cells were washed twice using PBS solution. Each material (p-coumaric acid, and anticoccidial agents, gallic acid, salinomycin: 10 ppm and diclazuril: 1 ppm) to the cells, and further cultured at a temperature of 40° C. for 24 hours.

The negative control group is MDBK cells infected by the protozoa, and the positive control group means a group in which salinomycin, gallic acid, or diclazuril solution was incubated with the protozoa. After removing the cells and protozoa inside the cells through pipetting, DNA was extracted from the cells using DNA extract kit (iNtRON Biotechnology), and PCR was performed using *E. tenella* ITS-1 (Internal transcribed spacer-1) gene-specific primers. The sequences of the used primers were described in Table 5 above. Ct values before/after washing for each material were compared and corrected with the ΔCt value of the negative control group to calculate the fold change ($2^{-\Delta Ct}$) at each time point compared to the control group, and the invasion inhibition rate (%) of the protozoa by material treatment was calculated, and the result was shown in Table 6 above.

As shown in Table 6 above, diclazuril showed an effect on intracellular protozoal propagation inhibition, and gallic acid showed an effect only on cell invasion of the protozoa, but on the other than, coumaric acid inhibited both cell invasion of the *Eimeria tenella* protozoan and intracellular protozoal propagation, and level thereof was more excellent than the positive control group. In addition, as shown in Table 7 above, in the coumaric acid treatment group, the cell invasion inhibition efficacy against *Eimeria acervulina* was more excellent than all the positive control groups (diclazuril, gallic acid and salinomycin).

Example 4. Anticoccidial Effect of Various Coumaric Acid Isomers

In the present example, for *Eimeria tenella*, which is most infected worldwide and has a high disease severity, the protozoa (sporozoite) direct killing ability of various coumaric acid isomers was evaluated, and using a representative animal cell known to be infected by *Eimeria*, an MDBK cell line, the intracellular protozoal invasion inhibition ability of various coumaric acid isomers was investigated.

Example 4-1. Direct Killing Effect Against *Eimeria* Protozoa

A certain amount of oocysts of the protozoa was put in a tube containing glass beads and pulverized, and then to remove the crushed oocyst cell wall and other debris, internal sporocysts were purified using the percoll density gradient, and washed with PBS solution. A reagent comprising sodium taurocholic acid (Sigma aldrich, USA) and trypsin (Gibco, USA), respectively, was treated to sporocysts of *Eimeria tenella* for excystation and they were incubated, and then they were washed with PBS solution once and protozoa were obtained.

After reacting 0.1% DMSO, m-coumaric acid (sigma, 14755-02-3), Caffeic acid (sigma, 331-39-5) and Ferulic acid (sigma, 1135-24-6) with the *Eimeria tenella* protozoa at a concentration of 10 ppm, respectively, only alive protozoa (sporozoites) were counted through microscopic observation. Then, the death rate (%) of the protozoa when each material was treated compared to the PBS-treated negative control group was measured, and the result was shown in Table 8 below.

TABLE 8

| sample | Dose (ppm) | Killed sporozoites % |
|---|---|---|
| Cell only | | 0 |
| 0.1% DMSO | | 0 |
| m-coumaric acid | 10 | 10.7 |
| Caffeic acid | 10 | 0 |
| Ferulic acid | 10 | 0 |

As shown in Table 8, at the same concentration, m-coumaric acid showed the direct killing effect against the *Eimeria* sp. protozoan more significantly excellently than Caffeic acid and Ferulic acid.

Example 4-2. Confirmation of Intracellular Protozoal Invasion Inhibition Ability By the similar method to Example 3-2 above, 0.1% DMSO, p-coumaric acid (sigma, CAS No. 501-98-4), m-coumaric acid (sigma, 14755-02-3), and o-coumaric acid (sigma, 614-60-8) were treated at a concentration of 10 ppm, respectively, and the cell invasion inhibition rate against the *Eimeria tenella* protozoan was measured, and the result was shown in Table 9.

TABLE 9

| sample | Dose (ppm) | Invasion inhibition % |
|---|---|---|
| Cell only | | 0 |
| 0.1% DMSO | | 0 |
| p-coumaric acid | 10 | 7.98 |
| m-coumaric acid | 10 | 29.78 |
| o-coumaric acid | 10 | 39.57 |

As shown in Table 9, it could be confirmed that all the p-coumaric acid, m-coumaric acid, and o-coumaric acid showed the intracellular protozoal invasion inhibitory effect of the *Eimeria tenella* protozoan.

From the above description, those skilled in the art to which the present application pertains will be able to understand that the present application may be embodied in other specific forms without changing the technical spirit or essential characteristics. In this regard, it should be understood that the examples described above are illustrative and not restrictive in all respects. The scope of the present application should be construed as including all changes or modifications derived from the meaning and scope of the claims to be described below and equivalent concepts rather than the detailed description above, in the scope of the present application.

The invention claimed is:

1. A method for treating coccidiosis, the method consisting essentially of administering an effective amount of a composition consisting essentially of a coumaric acid or a pharmaceutically acceptable salt thereof to an animal in need thereof, wherein the coumaric acid or the pharmaceutically acceptable salt thereof is the only active ingredient in the composition, the coumaric acid is m-coumaric acid, o-coumaric acid, or a combination thereof, and the effective amount of the coumaric acid or the pharmaceutically acceptable salt thereof in the composition is at a concentration of 1 ppm or more and 1000 ppm or less.

2. The method according to claim 1, wherein the coccidiosis is an *Eimeria* sp. protozoan.

3. The method according to claim 1, wherein the treating coccidiosis is at least one selected from the group consisting of the following (1) to (4):

(1) reduction of at least one selected from the group consisting of lesion score, fecal oocyst excretion amount and mortality;

(2) inhibition of weight loss due to coccidiosis;

(3) increase of an anticoccidial index (ACI); and (4) reduction of cell invasion of an *Eimeria* sp. protozoan, propagation of the protozoan in cells, or both of them.

4. The composition according to claim 1, wherein the composition is a feed additive.

5. A method for killing *Eimeria* sp. protozoan, or inhibiting cell invasion of *Eimeria* sp. protozoan, the method consisting essentially of administering an effective amount of a composition consisting essentially of a coumaric acid or a salt thereof to an animal in need thereof, wherein the coumaric acid or the salt thereof is the only active ingredient, the coumaric acid is m-coumaric acid, o-coumaric acid, or a combination thereof, and the effective amount of the coumaric acid or the salt thereof in the composition is at a concentration of 1 ppm or more and 1000 ppm or less.

6. The method according to claim 1, wherein the coumaric acid is m-coumaric acid.

7. The method according to claim 1, wherein the coumaric acid is o-coumaric acid.

8. The method according to claim 5, wherein the coumaric acid is m-coumaric acid.

9. The method according to claim 5, wherein the coumaric acid is o-coumaric acid.

10. The method according to claim 1, wherein the effective amount of the coumaric acid or the pharmaceutically acceptable salt thereof in the composition is at a concentration of 10 ppm or more and 500 ppm or less.

11. The method according to claim 1, wherein the coccidiosis is induced by an *Eimeria tenella.*

12. The method according to claim 1, wherein the coccidiosis is induced by an *Eimeria acervulina.*

13. The method according to claim 5, wherein the effective amount of the coumaric acid or the pharmaceutically acceptable salt thereof in the composition is at a concentration of 10 ppm or more and 500 ppm or less.

14. The method according to claim 5, wherein the coccidiosis is induced by an *Eimeria tenella.*

15. The method according to claim 5, wherein the coccidiosis is induced by an *Eimeria acervulina.*

16. The composition according to claim 5, wherein the composition is a feed additive.

* * * * *